(12) United States Patent
Thompson

(10) Patent No.: US 6,322,493 B1
(45) Date of Patent: Nov. 27, 2001

(54) EXPANDED CLITORAL SENSITIZING COMPOUNDS WITH METHODS AND APPARATUS FOR THE DELIVERY OF THESE COMPOUNDS

(75) Inventor: Ronald J. Thompson, Ft. Thomas, KY (US)

(73) Assignee: 40 J's LLC, Ft. Thomas, KY (US)

( * ) Notice: Subject to any disclaimer, the term of this patent is extended or adjusted under 35 U.S.C. 154(b) by 0 days.

(21) Appl. No.: 09/520,110

(22) Filed: Mar. 7, 2000

Related U.S. Application Data

(63) Continuation-in-part of application No. 09/469,959, filed on Dec. 21, 1999, which is a continuation-in-part of application No. 09/414,250, filed on Oct. 7, 1999, which is a continuation-in-part of application No. 09/340,227, filed on Jul. 7, 1999.

(51) Int. Cl.[7] ............................................. A61F 5/00
(52) U.S. Cl. ................................................. 600/38
(58) Field of Search ........................ 600/38, 29; 601/84; 514/573, 944, 945, 947, 953, 967, 258, 565; 544/256; 424/727, 728

(56) References Cited

U.S. PATENT DOCUMENTS 4,139,006 * 2/1979 Corey ..................................... 600/29
5,386,836 * 2/1995 Biswas ................................... 600/29
5,460,597 * 10/1995 Hopper ................................... 601/84
5,877,216 * 3/1999 Place et al. ........................... 514/573

OTHER PUBLICATIONS

Adam & Eve Pussylip Gloss, p. 38; Mar. 18, 1997.*
Adam & Eve, Deep Throat Gel, p. 19; Mar. 18, 1997.*
Adam & Eve, Midnight Fire Massage Lotion, p. 17; Mar. 18, 1997.*
Xandria Collection, Good Head Gel, p. 10; Summer 1997.*
Xandria Collection, I–D Flavor Lube, p. 18; Summer 1997.*
Xandria Collection, Making Love Flavored Massage Oil, p. 41; Summer 1997.*

* cited by examiner

Primary Examiner—Eric F. Winakur
Assistant Examiner—Brian Szmal
(74) Attorney, Agent, or Firm—Don Halgren

(57) ABSTRACT

The present invention comprises a method and apparatus such as a hand-manipulable, clitoral stimulant-applying applicator for use to apply a clitoral stimulating compound to the clitoral area of the human female. A reservoir in the apparatus is arranged for containment of a clitoral stimulating compound, with a clitoral stimulating compound in said reservoir. A removable cover is arranged on the reservoir to expose the compound to permit the compound to be applied topically.

19 Claims, 2 Drawing Sheets

EXPANDED CLITORAL SENSITIZING COMPOUNDS WITH METHODS AND APPARATUS FOR THE DELIVERY OF THESE COMPOUNDS

This is a continuation-in-part application of my earlier co-pending application Ser. No. 09/469,959 filed Dec. 21, 1999, which is a continuation-in-part application of co-pending application Ser. No. 09/414,250 filed Oct. 7, 1999 which is a continuation-in-part application of co-pending application Ser. No. 09/340,227 filed Jul. 7, 1999, each of which are incorporated herein by reference in their entirety.

BACKGROUND OF THE INVENTION

1. Field of the Invention

This invention relates to arrangements for the stimulation of females and more particularly to topical application of specialized stimulatory medicaments.

2. Prior Art

The unique properties of the clitoral sensitizing compounds described in my earlier co-pending patent application Ser. No. 09/469,959 encompasses the vasodilatation of clitoral blood vessels by the initial effect of menthol to facilitate and promote the absorption of L-arginine when topically applied to the mucous membrane of the clitoris. The L-arginine stimulates the nitric oxide synthase mediated production of nitric oxide to effect clitoral sensitivity, arousal, and erection by sustained vasodilatation. Both of these actions are specific to the topical application of the compound to the mucous membrane of the clitoris and presume an inert, non-active base or vehicle. In the menthol/L-arginine compound, the menthol actually acts as a vehicle to enhance the absorption of L-arginine.

BRIEF SUMMARY OF THE INVENTION

The present invention relates to alternate preparations of menthol and related cooling compounds that comprises a class of single-source of botanical or essential oils that can be used individually or as a combination of several oils such as: Peppermint oil; Cornmint oil; Eucalyptus oil; Citronella oil; Indian turpentine oil; Camphor oil and Cinnamon oil.

In fact, all of the botanicals listed by Steinberg in "Frequency Use of Botanicals," in *Cosmetics and Toiletries magazine*, Volume 113, October, 1998, (incorporated herein by reference) are members of this class of singe-source botanical or essential oils. Potentially, any of these referenced oils could evoke the menthol-like effect on the mucous membrane to facilitate or promote the topical absorption of L-arginine. In addition, known minor skin irritants can cause a profound reaction when topically applied to mucous membrane, such as redness, irritation, and reflex vasodilatation. This irritant reaction associated with vasodilatation shares some similarities with the menthol effect, and could quite effectively substitute for the menthol in promoting L-arginine absorption and actions. Salicylate and capsiatin are two of the commonly used minor skin irritants. Oil soluble vitamins (co-enzymes) A, D, or E, could also potentiate absorption of menthol, L-arginine, minor skin irritants, or any of the menthol-related cooling compounds. The oil soluble vitamins could be used to substitute for, or be used in addition to, any of the previously listed components in a topical clitoral sensitizing preparation.

The invention may further comprise alternate preparations for the base or the vehicle. Such biologically active agents (menthol or its substitutes) and L-arginine can be compounded in a non-biologically active base, or in a biologically active base that promotes absorption, a vehicle. Any base or vehicle is intended to liquefy at body heat and in the presence of moisture present in mucous membrane when topically applied to mucous membrane tissue. Campos and Eccleston is "Vitamin A Skin Penetration, "Cosmetics and Toiletries magazine, volume 113, July, 1998, describe and quantify how different vehicles influence and promote the hairy skin (keratinized stratified squamous epithelium) absorption of Vitamin A. Mucous membranes absorb solutions more readily than hairy skin, but display linear absorption potentials relative to the vehicles studies by Campos and Eccleston. An active vehicle may be engineered that synegistically functions to promote the absorption and actions of menthol, menthol-related compounds, biologically derived oils, minor skin irritants, oil soluble vitamins, Larginine, or any combination of these.

There are solid/liquid state dynamics for the topical delivery of clitoral sensitizing compounds which cover any of the potential compounds for topical application to sensitize the clitoris because they can have different solid/liquid states at ambient and at body temperatures. A solid compound, such as exemplified by the Chap Stick® Lip Balm, A. H. Robbins Company, of Richmond, Va., could be directly applied to the undercarriage of the clitoris, and liquefy at body temperature and in the moisture inherent in mucous membrane tissue. Liquefied compounds are readily absorbed, dependent on various other factors described. A gel/cream or liquid compound could be directly applied to the clitoris for topical absorption. Like the solid-state compound, the gel/cream must liquefy before absorption can be effected. The dynamics of how rapidly a compound transforms from a solid state or gel/cream state to a liquid state could be controlled to evoke an almost immediate effect, or a relatively delayed effect, before absorption of the compound.

A crystalline related dissolution may be different from the temperature related dissolution of a solid or a gel/cream. Small crystals of menthol, L-arginine, or any of the previously described components, may be suspended in a base vehicle. Their availability for absorption would depend on their dissolution from a crystalline state to a liquid state. The crystalline effect may be designed to control the rate of absorption: for instance, whether the compound were available for absorption immediately on application, or if a delayed, sustained absorption over a period of time were desired. Both of these parameters could allow the discrete, private application of the clitoral-sensitizing compound in anticipation of intercourse, without knowledge of the partner.

Because the clitoral-sensitizing compounds are also intended to function independently without the preferred intercourse-related physical stimulation of the clitoris as taught in my aforementioned patent application Ser. No. 09/414,250, 09/340,227 and 09/469,959, the menthol/L-arginine compounds may also be arranged to be available in various strength to address the needs of all women. The menthol may be compounded in multiple strengths, ranging from 0.1% to 5%, and any increment in between. The L-arginine may also be compounded in multiple strengths ranging from 1% to 10%. The spectrum of different strengths may be compounded into a single delivery system, such as lip balm, or alternatively, in all of the potential delivery systems: solid, gel/cream, and liquid.

A single use or a multiple use delivery systems comprising clitoralsensitizing preparations may be individually packaged within a small tube or packet for single use. Conversely, a multiple-dose reusable delivery system, like a tube of hand cream or toothpaste, or a stick of lip balm, may be packaged for personal use.

The apparatus and methods to deliver a topical preparation to the clitoris may be comprised of a solid or semi-solid compound that may be directly applied to the undercarriage of the clitoris regardless of the use of a single-or multiple-use delivery system. The clitoral contact area of the solid or semi-solid compound in one preferred embodiment will have a notch to increase the surface area and clitoral contact of the compound. The notch is arranged with a height of 0.5 to 2 centimeters, and a maximum width of 2 centimeters at the rim of the notch. A properly designed concave notch will topically apply the compound to the 180 degree undercarriage of the clitoris. With proper directions for use, the application surface will initially contact the vestibular tissue at the base of the clitoris, to spread the compound on the entire clitoris.

A gel/cream or liquid compound would be applied to the clitoris with the same motions, but would require a different type of application device. The gel/cream or liquid could be applied by "roller balls" like those used to apply viscous deodorants, by a sponge-type applicator, or by a brush type of system. Any of the delivery devices for gel/cream or liquids could be designed to increase the surface area of the applicator tip and generally use the concave notch described for the solid compounds. The gel/cream and liquid applicators would have either a single-use reservoir or a multi-use reservoir. All of the delivery devices would have a cap that would seal the device before the initial use, and protect the applicator tip from contamination before use. Multi-use devices would have a resealing cap.

The invention thus comprises a hand-manipulable, clitoral stimulant-applying applicator for use to apply a clitoral stimulating compound to the clitoral area of the human female, comprising: a reservoir for containment of a clitoral stimulating compound; a clitoral stimulating compound in said reservoir; and a removable cover on the reservoir to expose the compound to permit said compound to be applied topically. The cover may comprise a removable cap. The reservoir may comprise a tube and said cover. The compound may comprise a gel. The compound may comprise a cream. The compound may comprise a fluid liquid. The compound may comprise a semi-solid. The semi-solid compound may have a notch on its distalmost end to facilitate the application of the compound. The applicator may includes a brush thereon. The applicator may include a sponge thereon. The applicator may include a roller ball arrangement thereon. The compound may be comprised of a mixture of menthol and L-arginine. The compound may have components selected from the group consisting of: Peppermint oil, Cornmint oil, Eucalyptus oil, Citronella oil, Indian turpentine oil, Camphor oil and Cinnamon oils. The compound may have components selected from the group consisting of: Salicylate, capsiatin, and oil soluble vitamins (co-enzymes) of A, D, or E.

The invention also includes a method of sensitizing the clitoris of a human female, comprising the steps of: applying a compound of sensitizing agent to the clitoris; and selecting a component of said sensitizing agent from the group consisting of: Peppermint oil, Cornmint oil, Eucalyptus oil, Citronella oil, Indian turpentine oil, Camphor oil, Cinnamon oils, Salicylate, capsiatin, and oil soluble vitamins (co-enzymes) of A, D, or E. The steps may include placing the sensitizing agent in a reservoir of an applicator; arranging a cover on the applicator to protect the agent in the reservoir.

The applicator may include a brush. The applicator may include a roller at one end thereof. The applicator may include a sponge at one end thereof. The sensitizing agent comprises a semi-solid stick having a "V" notch on a distal end thereof to facilitate application of the agent to a clitoris.

BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Referring now to the invention and the drawings in detail, alternate preparations of menthol and related cooling compounds comprises a class of single-source of botanical or essential oils that can be used individually or as a combination of several oils such as: Peppermint oil; Cornnint oil; Eucalyptus oil; Citronella oil; Indian turpentine oil; Camphor oil and Cinnamon oils, as compounds of the present invention. Any of these referenced oils could evoke the menthol-like effect on the mucous membrane to facilitate or promote the topical absorption of L-arginine. Salicylate and capsiatin, two commonly used minor skin irritants and oil soluble vitamins (co-enzymes) A, D, or E, could also potentiate absorption of menthol, L-arginine, minor skin irritants, or any of the menthol-related cooling compounds. The oil soluble vitamins could be used to substitute for, or be used in addition to, any of the previously listed components in a topical clitoral sensitizing preparation. Such solid/liquid state dynamics for the topical delivery of clitoral sensitizing compounds which cover any of the potential compounds for topical application to sensitize the clitoris because they can have different solid/liquid states at ambient and at body temperatures.

A gel/cream or liquid compound could be directly applied to the clitoris for topical absorption. Like the solid-state compound, the gel/cream must liquefy before absorption can be effected. The dynamics of how rapidly a compound transforms from a solid state or gel/cream state to a liquid state could be controlled to evoke an almost immediate effect, or a relatively delayed effect, before absorption of the compound.

A crystalline related dissolution may be different from the temperature related dissolution of a solid or a gel/cream. Small crystals of menthol, L-arginine, or any of the previously described components, may be suspended in a base vehicle. Their availability for absorption would depend on their dissolution from a crystalline state to a liquid state. The crystalline effect may be designed to control the rate of absorption: for instance, whether the compound were available for absorption immediately on application, or if a delayed, sustained absorption over a period of time were desired. Both of these parameters could allow the discrete, private application of the clitoral-sensitizing compound in anticipation of intercourse, without knowledge of the partner.

Figure 1:
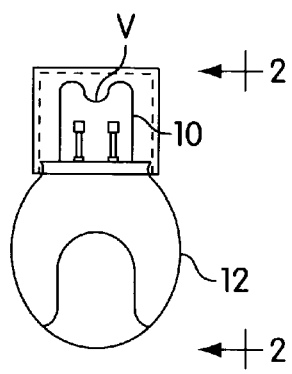
FIG. 1 is a front elevational view of a solid compound single-use applicator.
Figure 2:
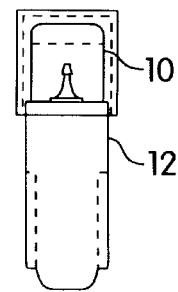
FIG. 2 is a view taken along the lines 2—2 of FIG. 1.
Figure 5:
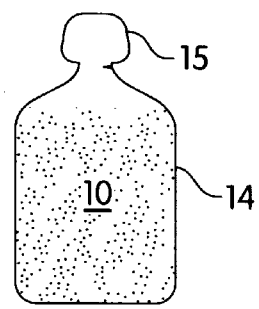
FIG. 5 is a front elevational view of a gel/cream/liquid compound single-use applicator.

A single use or a multiple use delivery systems comprising a clitoralsensitizing preparation 10 may be individually packaged within a small tube 12 or packet 14 for single use, as shown in FIGS. 1, 2 and 5. The tube 12 may be gripped by the thumb and first finger, and the compound preparation thereon applied as desired.

The packet 14 shown in FIG. 5 has a break-away seal 15 which permits the gel/cream or liquid 10 therein to be readily applied by merely squeezing the packet 14. Conversely, a multiple-dose reusable delivery system, like a tube of hand cream or toothpaste, or a stick of semi-solid compound, clitoral-sensitizing balm 16, may be packaged for personal use, as shown by the "lipstick-like" rotatively adjustable applicators 18 in FIGS. 3 and 4. This adjustable applicator 18 has a cap 20 to cover the balm compound 16.

Figure 3:
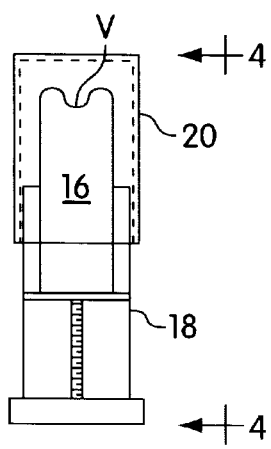
FIG. 3 is a front elevational view of a solid compound multiple-use applicator.
Figure 4:
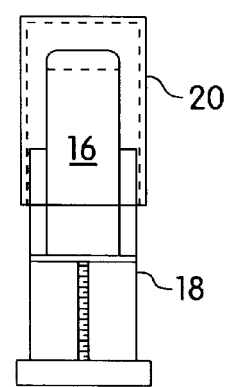
FIG. 4 is a view taken along the lines 4—4 of FIG. 3.
Figure 6:
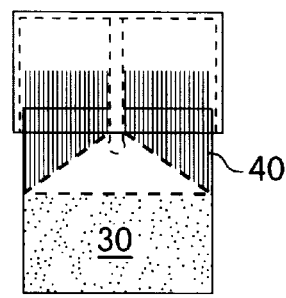
FIG. 6 is a front elevational view of a gel/cream/liquid compound single or multiple use brush applicator.
Figure 7:
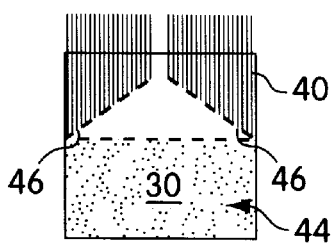
FIG. 7 is a view of the applicator shown in FIG. 6, with its cap off.
Figure 8:
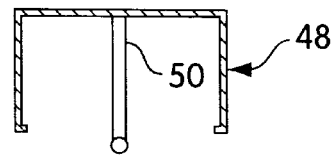
FIG. 8 is a side elevational view, in section, of the applicator cap shown in FIG. 6.
Figure 9:
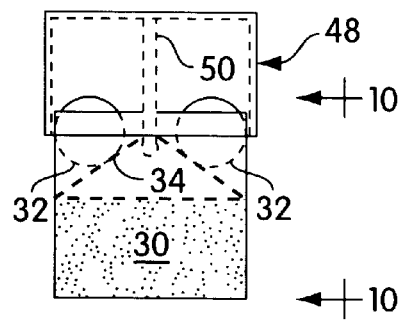
FIG. 9 is front elevational view of a gel/cream or liquid applicator with roller balls.
Figure 10:
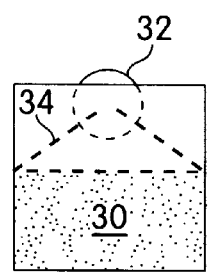
FIG. 10 is a view taken along the lines 10—10 of FIG. 9.

The apparatus and methods to deliver a topical preparation to the clitoris may also be comprised of a solid or semi-solid compound that may be directly applied to the undercarriage of the clitoris regardless of the use of a single-or multiple-use delivery system. The clitoral contact area of the solid or semi-solid compound in one preferred embodiment will have a notch "V" to increase the surface area and clitoral contact of the compound 16, as shown in FIGS. 1 and 3. The notch "V" is arranged with a height of 0.5 to 2 centimeters, and a maximum width of 2 centimeters at the rim of the notch "V". A properly designed concave notch "V" will topically apply the compound 16 to the 180 degree undercarriage of the clitoris. With proper directions for use, the application surface will initially contact the vestibular tissue at the base of the clitoris, to spread the compound on the entire clitoris. A gel/cream or liquid compound 30 of the present invention would be applied to the clitoris with the same motions, but would require a different type of application device. The gel/cream or liquid compound 30 may be applied by "roller balls" 32 like those used to apply viscous deodorants, as shown in FIGS. 9 and 10, supported within a foraminous top 34, covered when not needed, by a cap 46. The gel/cream or liquid compound 30 may also be applied by a sponge or brush 40 secured to a top 42 in a reservoir 44, as shown in FIGS. 6 and 7. A cap 48, shown also in FIG. 8 may include a removable seal 50, both of which are arranged to be removable to expose the sponge or brush 40 and openings 46 in the reservoir 44 to supply the fluid compound thereto. Any of the delivery devices for gel/cream or liquids could be designed to increase the surface area of the applicator tip and generally use the concave notch described for the solid compounds. The gel/cream and liquid applicators would have either a single-use reservoir or a multi-use reservoir. All of the delivery devices would have a cap "C" that would seal the device before the initial use, and protect the applicator tip from contamination before use. Multi-use devices, such as shown in FIGS. 3, 4, 6, 7 and 9 would have the resealing cap 48 for their protection.

I claim:

1. A hand-manipulable, clitoral stimulant container for use to apply a clitoral stimulating compound to the clitoral area of the human female, comprising:

a reservoir for containment of a clitoral stimulating compound;

a clitoral stimulating compound comprised of menthol and L-arginine disposed in said reservoir; and a removable end portion on said container to expose said compound to permit said compound to be applied topically.

2. The hand-manipulable, clitoral stimulant container as recited in claim 1, wherein said end portion comprises a removable cap.

3. The hand-manipulable, clitoral stimulant container as recited in claim 1, wherein said reservoir comprises a tube and said end portion.

4. The hand-manipulable, clitoral stimulant container as recited in claim 1, wherein said compound comprises a gel.

5. The hand-manipulable, clitoral stimulant container as recited in claim 1, wherein said compound comprises a cream 6. The hand-manipulable, clitoral stimulant container as recited in claim 1, wherein said compound comprises a fluid liquid.

7. The hand-manipulable, clitoral stimulant container as recited in claim 1, wherein said compound comprises a semi-solid.

8. The hand-manipulable, clitoral stimulant container as recited in claim 7, wherein said semi-solid compound has a notch on its distalmost end to facilitate the application of said compound.

9. The hand-manipulable, clitoral stimulant container as recited in claim 6, wherein said container comprises an applicator which includes a brush thereon.

10. The hand-manipulable, clitoral stimulant container as recited in claim 6, wherein said container comprises an applicator which includes a sponge thereon.

11. The hand-manipulable, clitoral stimulant container as recited in claim 6, wherein said container comprises an applicator which includes a roller ball arrangement thereon.

12. The hand-manipulable, clitoral stimulant container as recited in claim 1, wherein said compound has components selected from the group consisting of: Peppermint oil, Cornirnint oil, Eucalyptus oil, Citronella oil, Indian turpentine oil, and Camphor oil.

13. The hand-manipulable, clitoral stimulant container as recited in claim 1, wherein said compound has components selected from the group consisting of: Salicylate, capsiatin, and oil soluble vitamins (co-enzymes) of A, D, or E.

14. A method of sensitizing the clitoris of a human female, comprising the steps of:

applying a compound of sensitizing agent to said clitoris; and selecting a component of said sensitizing agent from the group consisting of: Peppermint oil, Cornmint oil, Eucalyptus oil, Citronella oil, Indian turpentine oil, Camphor oil, menthol and L-arginine, Salicylate, capsiatin, and oil soluble vitamins (co-enzymes) of A, D, or E.

15. The method of sensitizing the clitoris of a human female as recited in claim 14, comprising the steps of:

placing said sensitizing agent in a reservoir of an applicator;

arranging a cover on said applicator to protect said agent in said reservoir.

16. The method of sensitizing the clitoris of a human female as recited in claim 15, wherein said applicator includes a brush.

17. The method of sensitizing the clitoris of a human female as recited in claim 15, wherein said applicator includes a roller at one end thereof.

18. The method of sensitizing the clitoris of a human female as recited in claim 15, wherein said applicator includes a sponge at one end thereof.

19. The method of sensitizing the clitoris of a human female as recited in claim 14, wherein said sensitizing agent comprises a semi-solid stick having a "V" notch oln a distal end thereof to facilitate applicatin of said agen to a clitoris.

* * * * *